US012582124B2

(12) United States Patent
Jiang et al.

(10) Patent No.: US 12,582,124 B2
(45) Date of Patent: Mar. 24, 2026

(54) PARABURKHOLDERIA SP. AND USE THEREOF

(71) Applicant: Institute of Applied Ecology, Chinese Academy of Sciences, Liaoning (CN)

(72) Inventors: Nan Jiang, Liaoning (CN); Jingmin Hu, Liaoning (CN); Yulan Zhang, Liaoning (CN); Zhenhua Chen, Liaoning (CN); Lijun Chen, Liaoning (CN)

(*) Notice: Subject to any disclaimer, the term of this patent is extended or adjusted under 35 U.S.C. 154(b) by 0 days.

(21) Appl. No.: 18/772,054

(22) Filed: Jul. 12, 2024

(65) Prior Publication Data

US 2024/0423213 A1    Dec. 26, 2024

(30) Foreign Application Priority Data

May 24, 2023    (CN) .......................... 202310594019.2

(51) Int. Cl.
| | |
|---|---|
| A01N 63/20 | (2020.01) |
| A01P 3/00 | (2006.01) |
| C12N 1/20 | (2006.01) |
| C12R 1/00 | (2006.01) |

(52) U.S. Cl.
CPC ................ A01N 63/20 (2020.01); A01P 3/00 (2021.08); C12N 1/20 (2013.01); C12R 2001/00 (2021.05)

(58) Field of Classification Search
CPC ...................................................... A01N 63/20
See application file for complete search history.

(56) References Cited

U.S. PATENT DOCUMENTS

2023/0088888 A1    3/2023    Zhong et al.

FOREIGN PATENT DOCUMENTS

| | | |
|---|---|---|
| CN | 110438037 A | 11/2019 |
| CN | 110669686 A | 1/2020 |
| CN | 114196582 A | 3/2022 |

OTHER PUBLICATIONS

T. Li (AnHui Agricultural University, He Fei, China), GenBank Record No. MW193377, hit No. 1 in a search of GenEmbl on Jan. 27, 2025, 2020.*

(Continued)

*Primary Examiner* — Rosanne Kosson

(74) *Attorney, Agent, or Firm* — Hawaii Patent Services; Nathaniel K. Fedde; Kenton N. Fedde

(57) ABSTRACT

The present invention provides *Paraburkholderia* sp. LSOJM18 and use thereof as well as a microbial inoculum, belonging to the technical field of microorganisms. The *Paraburkholderia* sp. LSOJM18 was deposited to the China Center for Type Culture Collection on Dec. 29, 2022, with the depository number CCTCCNO: M20222102. With a strong phosphate solubilization capacity, the strain provided by the present invention is suitable for activating phosphorus in farmland soil. Using the phosphate-solubilizing bacteria can significantly increase the available phosphorus content of soil and reduce the application of chemical phosphate fertilizers. Acting on a wide range of substrates, the phosphate-solubilizing bacteria strain provided by the present invention can not only secrete phosphatase to hydrolyze organic phosphorus, but also release small molecules such as organic acids, etc., to activate the fixed inorganic phosphorus, and using the phosphate-solubilizing bacteria can significantly improve the phosphorus activation capacity of soil.

1 Claim, 3 Drawing Sheets

Specification includes a Sequence Listing.

(56) References Cited

OTHER PUBLICATIONS

"Optimization of fermentation conditions for the red pigment branch of Sporidiobolus pararoseus and key enzyme gene transcription level analysis" Huang Tao, "China's Outstanding Master's Thesis Database, Issue 4"; Apr. 15, 2021; pp. 23-26, 30; Claims 1-8.

* cited by examiner

PARABURKHOLDERIA SP. AND USE THEREOF

CROSS-REFERENCE TO RELATED APPLICATIONS

This application claims priority of Chinese Patent Application No. 202310594019.2, filed on May 26, 2023, the entire contents of which are incorporated herein by reference.

SEQUENCE LISTING

The instant application contains a Sequence Listing with 1 sequence, which has been submitted electronically in XML format and is hereby incorporated herein by reference in its entirety. Said XML copy, created on Jul. 12, 2024 is named BJWCHC-US-1-02-Sequence Listings.xml, and is 4 kbytes in size.

TECHNICAL FIELD

The present invention relates to the field of microorganisms, and in particular to *Paraburkholderia* sp. LSOJM18 and use thereof.

BACKGROUND

The application of a phosphate fertilizer is one of the necessary measures to ensure the yield of farmland crops. However, 75-90% of the applied phosphate fertilizer is fixed in the soil and cannot be utilized. A large amount of phosphorus accumulates in the soil in unavailable forms, significantly affecting the soil nutrient structure and increasing the risk of non-point source pollution at the same time. More importantly, a phosphate rock, the main source of the phosphate fertilizer, is a non-renewable resource. There is an urgent need for an effective soil phosphorus activation technology to activate and efficiently utilize the phosphorus accumulated in the soil, taking into account the sustainable utilization of agricultural production, phosphate rock resources and phosphorus.

Phosphate-solubilizing microorganisms have the ability of dissolving the insoluble phosphorus in soil, reducing phosphate fertilizer fixation, and increasing the phosphorus uptake by crops, thus improving the phosphate fertilizer utilization rate and crop yield, which is currently a safe, economical and effective biological measure recognized in the world. However, highly efficient phosphate-solubilizing microbial strains that can be obtained through isolation have limited types and quantities, more screening and a poor adaptability to soils in different environments. Therefore, regionally suitable phosphate-solubilizing microbial resources and utilization thereof are of important strategic significance to activate phosphorus in soil, guarantee a grain yield, and reduce an environmental pollution and an energy waste.

SUMMARY

In order to solve the above problems, the present invention provides *Paraburkholderia* sp. LSOJM18 and use thereof. With a strong phosphate solubilization capacity, the strain provided by the present invention is suitable for activating phosphorus in farmland soil, and using the phosphate-solubilizing bacteria can significantly increase the available phosphorus content of soil and reduce the application of phosphate fertilizers.

In order to achieve the above objective, the present invention adopts the following technical solution:

The present invention provides *Paraburkholderia* sp. LSOJM18, which was deposited to the China Center for Type Culture Collection on Dec. 29, 2022, with the depository number CCTCCNO: M20222102.

The present invention further provides use of the *Paraburkholderia* sp. LSOJM18 described in the above technical solution in solubilizing and decomposing phosphorus.

Preferably, the phosphorus in the solubilized and decomposed phosphorus includes inorganic phosphorus and/or organic phosphorus.

Preferably, the inorganic phosphorus includes calcium phosphate.

Preferably, a culture medium containing the calcium phytate uses water as a solvent and includes: 10 g/L of glucose, 3 g/L of calcium phytate, 5 g/L of $MgCl_2$, 0.25 g/L of $MgSO_4 \cdot 7H_2O$, 0.2 g/L of KCl and 0.1 g/L of $(NH_4)_2SO_4$.

Preferably, the organic phosphorus includes calcium phytate.

Preferably, a culture medium containing the calcium phosphate uses water as a solvent and includes: 10 g/L of glucose, 5 g/L of $Ca_3(PO_4)_2$, 5 g/L of $MgCl_2$, 0.25 g/L of $MgSO_4 \cdot 7H_2O$, 0.2 g/L of KCl and 0.1 g/L of $(NH_4)_2SO_4$.

The present invention further provides a microbial inoculum for solubilizing and decomposing phosphorus, wherein the bacterial content of the *Paraburkholderia* sp. in the microbial inoculum described in the above technical solution is $1 \times 10^9$ CFU/mL.

The beneficial effects of the present invention are as follows:

With a strong phosphate solubilization capacity, the strain provided by the present invention is suitable for activating phosphorus in farmland soil, and using the phosphate-solubilizing bacteria can significantly increase the available phosphorus content of soil and reduce the application of phosphate fertilizers.

Acting on a wide range of substrates, the phosphate-solubilizing bacteria strain provided by the present invention can not only secrete phosphatase to hydrolyze organic phosphorus, but also release small molecules such as organic acids, etc., to activate the fixed inorganic phosphorus, and using the phosphate-solubilizing bacteria can significantly improve the phosphorus activation capacity of soil.

The phosphate-solubilizing bacterium *Paraburkholderia* sp. LSOJM18 provided by the present invention has a phosphate-decomposing index of 1.81 and a phosphate-decomposing amount of 210 mg/L after being cultured in a calcium phytate (organic phosphorus) solid medium for 5 days.

The phosphate-solubilizing bacterium *Paraburkholderia* sp. LSOJM18 provided by the present invention has a phosphate-solubilizing index of 1.10 and a soluble phosphorus concentration up to 339 mg/L after being cultured in a calcium phosphate (inorganic phosphorus) solid medium for 5 days.

After the *Paraburkholderia* sp. LSOJM18 provided by the present invention is prepared as a microbial inoculum, it can be used as a phosphorus synergistic agent, an activator and an agricultural microbial inoculum. The application of the phosphate-solubilizing bacterium combined with a chemical fertilizer can increase available phosphorus content of soil and fertilizer utilization efficiency, thus reducing the application of phosphate fertilizers by 20% and still ensuring an increase in crop yields by 4.6%, with the available phosphorus contents in the surface soil (0-10 cm) and surface layer (10-20 cm) increased by 9.0% and 12.6%, respectively.

Description of Microbial Preservation

The *Paraburkholderia* sp. LSOJM18 was deposited to the China Center for Type Culture Collection on Dec. 29, 2022, with the depository number CCTCCNO: M20222102, deposit address: Wuhan University.

DETAILED DESCRIPTION

Figure 1A:
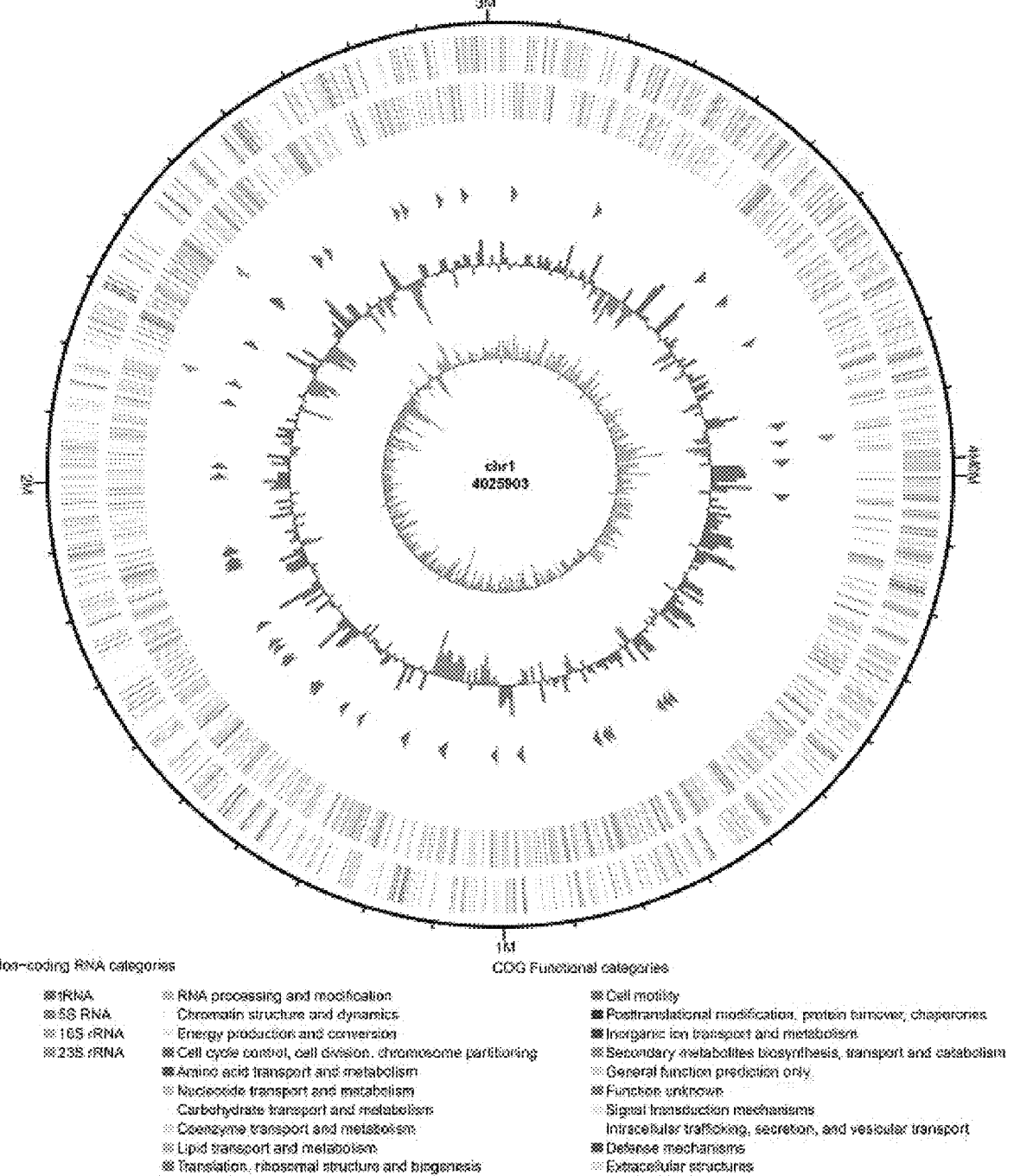
FIG. 1*a* shows a genome sequencing complete map and a genome complete map (chromosome 1) of *Paraburkholderia* sp. LSOJM18.
Figure 1B:
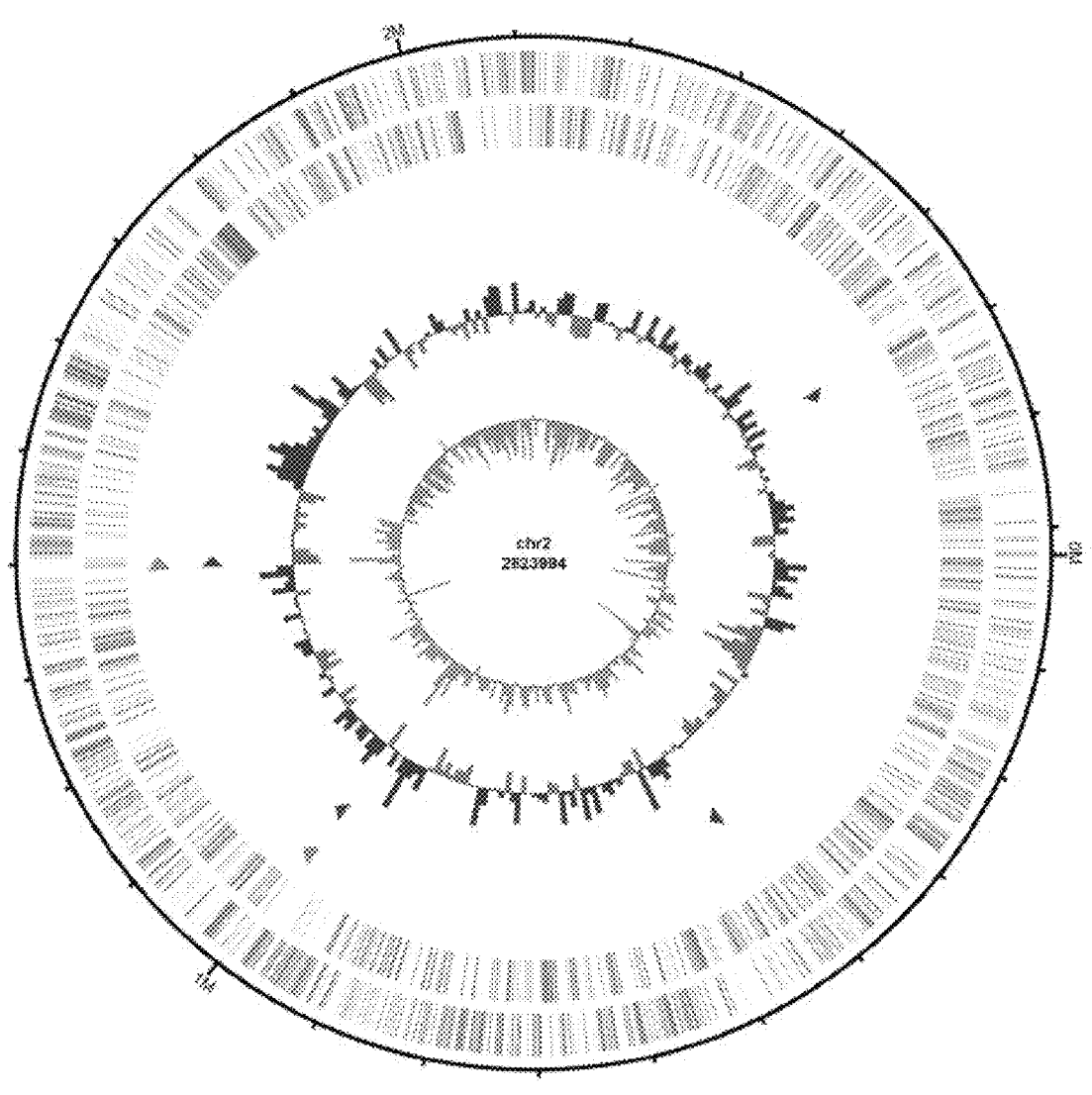
FIG. 1*b* shows a genome sequencing complete map and a genome complete map (chromosome 2) of *Paraburkholderia* sp. LSOJM18.
Figure 2:
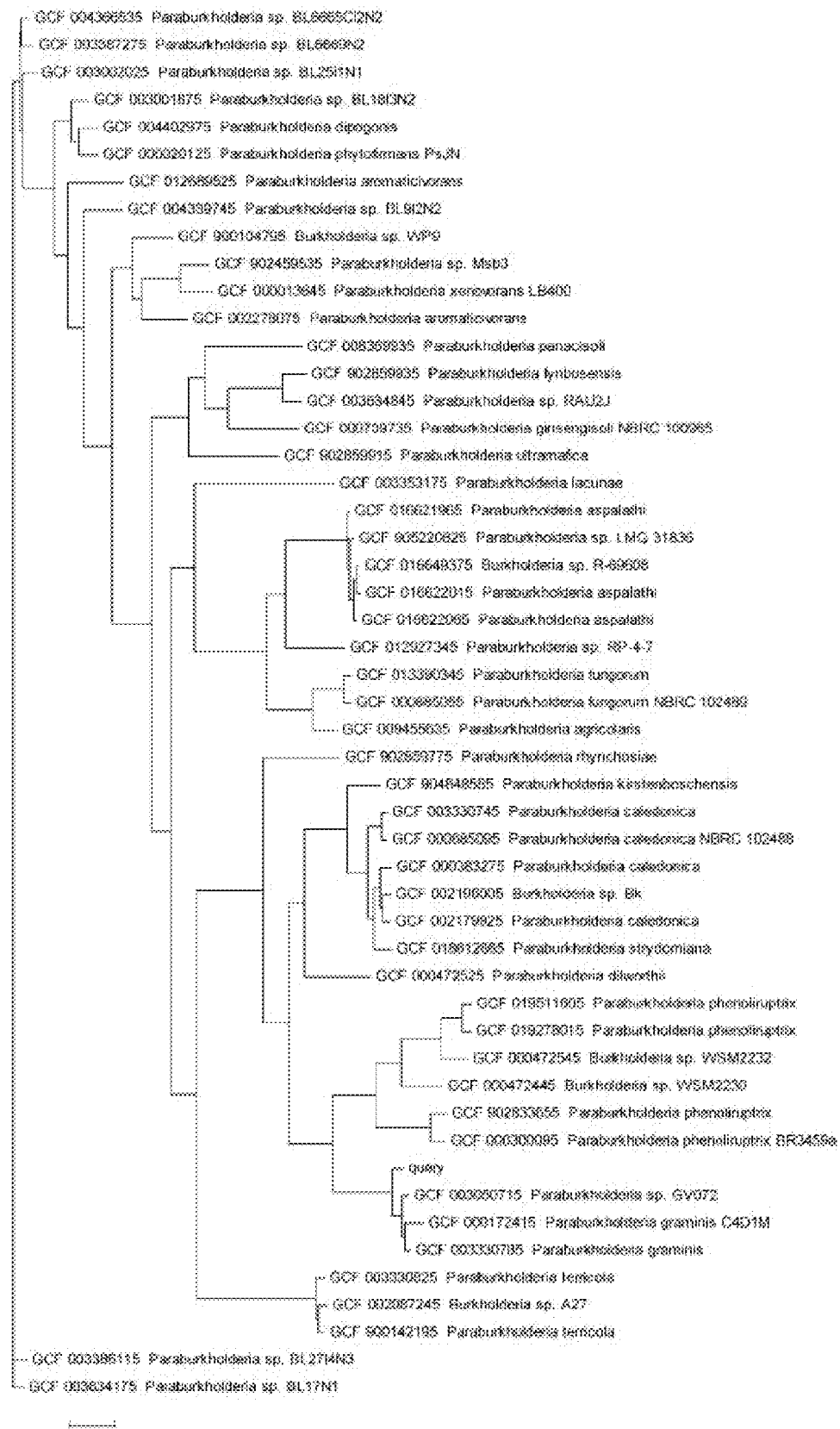
FIG. 2 shows an evolutionary tree constructed using the Maximum likelihood method based on 130 housekeeping genes.

The present invention provides *Paraburkholderia* sp. LSOJM18, which was deposited to the China Center for Type Culture Collection on Dec. 29, 2022, with the depository number CCTCCNO: M20222102.

The present invention further provides use of the *Paraburkholderia* sp. LSOJM18 described in the above technical solution in solubilizing and decomposing phosphorus. In the present invention, the phosphorus in the solubilized and decomposed phosphorus preferably includes organic phosphorus and/or inorganic phosphorus. In the present invention, the organic phosphorus preferably includes calcium phytate, and a culture medium containing the calcium phytate uses water as a solvent and preferably includes: 10 g/L of glucose, 3 g/L of calcium phytate, 5 g/L of $MgCl_2$, 0.25 g/L of $MgSO_4 \cdot 7H_2O$, 0.2 g/L of KCl and 0.1 g/L of $(NH_4)_2SO_4$. In the present invention, the inorganic phosphorus includes calcium phosphate, and a culture medium containing the calcium phosphate uses water as a solvent and preferably includes: 10 g/L of glucose, 5 g/L of $Ca_3(PO_4)_2$, 5 g/L of $MgCl_2$, 0.25 g/L of $MgSO_4 \cdot 7H_2O$, 0.2 g/L of KCl and 0.1 g/L of $(NH_4)_2SO_4$.

The present invention further provides a microbial inoculum for solubilizing and decomposing phosphorus, wherein the bacterial content of the *Paraburkholderia* sp. in the microbial inoculum described in the above technical solution is $1 \times 10^9$ CFU/mL.

In order to further illustrate the present invention, the present invention will be described in detail below in conjunction with the examples, however they should not be understood as limiting the scope of protection of the present invention.

Example 1

1. Strain Screening and Preservation (1) The surface soil from corn farmland in Lishu County, Siping City, Jilin Province was collected, and placed in sterile bags for low temperature preservation.

(2) 1 g of soil was added in 100 mL of organic phosphorus screening liquid medium (glucose: 10 g/L, calcium phytate: 3 g/L, $MgCl_2$: 5 g/L, $MgSO_4 \cdot 7H_2O$: 0.25 g/L, KCl: 0.2 g/L, $(NH_4)$ $2SO_4$: 0.1 g/L), then placed in a thermostatic incubator at 28° C. for cultivation with shaking 24 hours.

4

(3) 1 mL of culture suspension was taken and inoculated to 100 mL of freshly prepared organic phosphorus screening liquid medium, then placed in a thermostatic incubator at 28° C. for cultivation with shaking 24 hours.

(4) After step (3) was repeated once, the culture suspension was taken and subjected to 104- and 105-fold gradient dilution, 200 μL of which was taken and coated onto an organic phosphorus screening liquid medium plate, then placed in a thermostatic incubator at 28° C. for cultivation 24 hours to 48 hours.

(5) A strain with a larger transparent circle (i.e. phosphate-solubilizing circle) was selected and named as LSOJM18, then a phosphate-solubilizing index (diameter of phosphate-solubilizing circle/diameter of bacterial colony) was calculated. The strain was purified on the organic phosphorus screening plate, followed by monoclonal purification at least 3 times. The purified strains were mixed with a fresh bacterial solution at a ratio of 1:1 by 50% glycerol and preserved in an ultra-low temperature freezer at −80° C.

2. Identification of Strains

The total deoxyribonucleic acid (DNA) of strain LSOJM18 was extracted with a bacterial genomic DNA rapid extraction kit, and the concentration and purity of the extracted DNAs were detected by Qubit2.0. The DNA was used as a template and 16S rRNA 27F/1429R was used as a primer for a polymerase chain reaction (PCR). Conditions for PCR reaction: pre-denaturation at 95° C. for 5 minutes; denaturation at 95° C. for 30 seconds, annealing at 56° C. for 30 seconds, extension at 72° C. for 90 seconds, 30 cycles; extension at 72° C. for 10 minutes. After the quality of the PCR amplification product was detected by 1.5% agarose gel electrophoresis, amplified fragments were sequenced using the Sanger method, and the 16S rRNA sequence of the strain is as shown in SEQ ID NO. 1.

The sequence was subjected to comparative analysis with the 16S rRNA database of National Center of Biotechnology Information (NCBI), and LSOJM18 was identified as *Paraburkholderia* sp.

```
>16S rRNA sequence of Paraburkholderia sp.
LSOJM18 strain (SEQ ID NO. 1):
TGCATGCGCATGCTTACCATGCAGTCGAACGGCAGCACGGGAGCAA

TCCTGGTGGCGAGTGGCGAACGGGTGAGTAATACATCGGAACGTG

TCCTGTAGTGGGGGATAGCCCGGCGAAAGCCGGATTAATACCGCA

TACGCTCTGCGGAGGAAAGCGGGGGATCCTTCGGGACCTCGCGCT

ACAGGGGCGGCCGATGGCAGATTAGCTAGTTGGTGGGGTAAAGGC

CTACCAAGGCGACGATCTGTAGCTGGTCTGAGAGGACGACCAGCC

ACACTGGGACTGAGACACGGCCCAGACTCCTACGGGAGGCAGCAG

TGGGGAATTTTGGACAATGGGCGCAAGCCTGATCCAGCAATGCCG

CGTGTGTGAAGAAGGCCTTCGGGTTGTAAAGCACTTTTGTCCGGA

AAGAAACCGCCTGGCTAATATCCGGGTGGGATGACGGTACCGGA

AGAATAAGCACCGGCTAACTACGTGCCAGCAGCCGCGGTAATACG

TAGGGTGCAAGCGTTAATCGGAATTACTGGGCGTAAAGCGTGCGC

AGGCGGTTCGCTAAGACAGATGTGAAATCCCCGGGCTTAACCTGG

GAACTGCATTTGTGACTGGCGGGCTAGAGTATGGCAGAGGGGGGT

AGAATTCCACGTGTAGCAGTGAAATGCGTAGAGATGTGGAGGAAT
```

-continued
```
ACCGATGGCGAAGGCAGCCCCCTGGGCCAATACTGACGCTCATGC

ACGAAAGCGTGGGGAGCAAACAGGATTAGATACCCTGGTAGTCCA

CGCCCTAAACGATGTCAACTGGTTGTCGGGCCTTCATTGGCTTGG

TAACGTAGCTAACGCGTGAAGTTGACCGCCTGGGGAGTACGGTCG

CAAGATTAAAACTCAAAGGAATTGACGGGGACCCGCACAAGCGGT

GGATGATGTGGATTAATTCGATGCAACGCGAAAAACCTTACCTAC

CCTTGACATGTACGGAACCCTGCTGAGAGGTGGGGGTGCCCGAAA

GGGAGCCGTAACACAGGTGCTGCATGGCTGTCGTCAGCTCGTGTC

GTGAGATGTTGGGTTAAGTCCCGCAACGAGCGCAACCCTTGTCCC

TAGTTGCTACGCAAGAGCACTCCAGGGAGACTGCCGGTGACAAAC

CGGAGGAAGGTGGGGATGACGTCAAGTCCTCATGGCCCTTATGGG

TAGGGCTTCACACGTCATACAATGGTCGGAACAGAGGGTCGCCAA

GCCGCGAGGTGGAGCCAATCCCAGAAAACCGATCGTAGTCCGGAT

CGCACTCTGCAACTCGAGTGCGTGAAGCTGGAATCGCTAGTAATC

GCGGATCAGCATGCCGCGGTGAATACGTTCCCGGGTCTTGTACAC

ACCGCCCGTCACACCATGGGAGTGGGTTTTACCAGAAGTGGCTAG

TCTAACCGCAAGGAGGACGGTCACCACGGTAGATCAGGTCA.
```

Example 2

Whole Genome Sequencing of Strain TELL-Seq (1) Extraction of genomic DNA: high quality of genomic DNA was extracted from soil samples, the integrity of the extracted DNA was detected by agarose gel electrophoresis, the DNA concentration was accurately quantified by Qubit fluorometer, and the purity of DNA was detected by Nano-Drop (OD260/OD280).

(2) Construction of sequencing library: the high quality of genomic DNA was treated with the TELL-Seq™ WGS Library Prep kit (UST Company). First, the long fragments of DNA were specifically labeled by combining the innovative transposase of microbeads, and then the DNA was cleaved by transposase and exonuclease, and ligated with a linker to form libraries of different fragment sizes. The microbeads were subjected to library amplification after being washed, the i5Index sequence was added, and finally the magnetic beads were washed to form a qualified library. The library concentration was detected by Qubit, and the library fragment length was detected by an Agilent fragment analyzer to ensure the library quality.

(3) On-machine sequencing: the qualified libraries were detected, and the libraries were subjected to PE150 paired-end sequencing using a high-throughput sequencing platform.

(4) Quality control and filtering of raw sequencing data: raw sequencing data were subjected to quality inspection using FastQC software (v0.11.9), including basic statistical information, distribution of each base position, proportion distribution of adenosine thymine cytosine guanine (ATCG), guanine and cytosine (GC) content distribution, sequencing read length distribution, repetition level assessment, and proportion of linker sequences; the sequencing linkers in the raw sequencing data were sheared using the Cutadapt software (v1.0.3), meanwhile the sequences with a high proportion of low-quality bases and ambiguous bases, as well as incorrect labels and corresponding sequences were removed, the remaining high-quality data (clean reads) were used for subsequent bioinformatics analysis.

(5) Genome assembly and evaluation: the data after quality control was assembled with Tell-Link to obtain a scaffold sequence, which was verified with the GapCloser (v1.12) software; the assembled sequences were subjected to statistics of GC content and sequence coverage depth, which should exhibit a Poisson distribution ideally.

(6) Non-coding ribonucleic acid (RNA) and gene prediction: the rRNA and tRNA contained in the genome were predicted with the barmap (0.9) and ARAGORN (v1.2.41) software; and the bacteria were subjected to gene prediction with the PRODIGAL (v2.6.3).

(7) Gene function annotation: the protein sequences of the predicted genes were subjected to blastp comparison with non-redundant (NR), gene ontology (GO), cluster of orthologous (COG), kyoto encyclopedia of genes and genomes (KE GG) and Swiss-Prot databases (BLAST+ 2.7.1, alignment standard: E value≤1e-5), to obtain the annotation information of the predicted genes.

(8) Genome complete map: genomic cycle map was plotted with Circos software (v0.64) to comprehensively display the genome characteristics, including information such as distribution of genes on the sense and antisense strands, the COG functional classification of genes, GC content, genomic islands, and homologous genes, etc., and have more comprehensive and intuitive understandings on the genome characteristics of strains.

(9) Construction of evolutionary tree: 130 housekeeping genes were selected, and used to construct the evolutionary tree with RaxML software by the maximum likelihood method.

Example 3

Determination of Phosphate Solubilization Capacity (Phosphate-Decomposing Amount):

(1) Formulation of bacterial suspension: one loop of the bacterial inoculum preserved in example 1 was picked with an inoculating loop, and inoculated into a test tube containing Luria-Bertani (LB) culture medium, and cultured overnight with shaking at a constant temperature of 28° C. Then, an amount of 2% of the inoculum was transferred into an Erlenmeyer flask containing LB culture medium, and cultured with shaking at a constant temperature of 28° C. until OD600 of the bacterial suspension was about 1.0.

(2) Cultivation: 1 mL of bacterial suspension was aspirated and placed in 1.5 mL of centrifuge tube, washed 3 times with sterile water, and resuspended in sterile water.

(3) 0.2 mL of the washed bacterial suspension (inoculum size: 1%) was aspirated, then transferred to a container containing 20 mL of liquid culture medium (determination of organic phosphorus solubilization capacity: the organic phosphorus screening liquid medium was the same as example 1; determination of inorganic phosphorus solubilization capacity: calcium phosphate culture medium (glucose: 10 g/L, $Ca_3(PO_4)_2$: 5 g/L, $MgCl_2$: 5 g/L, $MgSO_4 \cdot 7H_2O$: 0.25 g/L, KCl: 0.2 g/L, $(NH_4)_2SO_4$: 0.1 g/L)), incubated at a constant temperature of 28° C. for 7 days, 3 parallels were set up, and sampled every 24 hours; at the same time, 0.2 mL of sterile water was aspirated to replace the bacterial suspension, and used as a negative control.

(4) it was stood still at a room temperature for 15 minutes, the fermentation liquid was poured into a centrifuge tube, centrifuged at 1,500 rpm for 3 minutes, the supernatant A was collected; a part of the supernatant A was centrifuged again at 10,000 rpm for 10 minutes, and supernatant B was collected.

(5) Determination of concentration of bacterial solution: 100 µL of supernatant A was aspirated, and 100 µL of 1M HCl was added, and the OD 600 value was measured with a spectrophotometer.

(6) Determination of available phosphorus:

An appropriate amount of supernatant B was aspirated and placed in a 50 mL of volumetric flask, 8 mL of molybdenum antimony anti-chromogenic solution was added and the volume was adjusted to 50 mL with deionized water, the solution was shaken well, and the absorbance of the solution was measured at 880 nm with a spectrophotometer after color development.

Molybdenum antimony anti-chromogenic solution: 0.528 g of ascorbic acid was dissolved in 100 mL of molybdenum antimony sulfate stock solution and mixed evenly. This solution should be prepared freshly. Molybdenum antimony sulfate stock solution: 6.0 g of the finely ground ammonium molybdate was weighed and dissolved in 200 mL of water; 0.146 g of antimony potassium tartrate was weighed and dissolved in 50 mL of water; 74 mL of concentrated sulfuric acid was measured and slowly added to 400 mL of water with stirring continuously, then cooled down; the above three solutions were mixed slowly, then cooled down, water was added to dilute and the volume was adjusted to 1,000 mL, the solution was shaken well and stored in a brown reagent bottle for later use.

Standard curve plotting: 0 mL, 1 mL, 2 mL, 4 mL, 6 mL, 8 mL, and 10 mL of the 5 mg/L phosphorus standard solution were accurately aspirated into 50 mL of volumetric flasks, respectively, 5 mL of molybdenum antimony anti-chromogenic solution was added, and the volume was adjusted to 50 mL with water. The solution was shaken well, and after color development, and the absorbance of the solution was measured at 880 nm with a spectrophotometer after color development.

$$\text{Phosphate-decomposing amount (mg/L)} = \rho \times V2/V1$$

In the formula: $\rho$-mass concentration of phosphorus in the solution to be tested (mg/L);

V1—the aspirated volume of supernatant B (mL);

V2—the volume of the color developed solution (mL).

(7) Determination of pH value: the pH value of supernatant B was measured with a pH meter.

The results are as follows:

The phosphate-solubilizing bacterium *Paraburkholderia* sp. LSOJM18 had a phosphate-decomposing index of 1.81 and a phosphate-decomposing amount of 210 mg/L after being cultured in a calcium phytate (organic phosphorus) solid medium for 5 days.

The phosphate-solubilizing bacterium *Paraburkholderia* sp. LSOJM18 had a phosphate-solubilizing index of 1.10 and a soluble phosphorus concentration up to 339 mg/L after being cultured in a calcium phosphate (inorganic phosphorus) solid medium for 5 days.

Thus, it can be concluded that, acting on a wide range of substrates, the phosphate-solubilizing bacteria strain provided by the present invention can not only secrete phosphatase to hydrolyze organic phosphorus, but also release small molecules such as organic acids, etc., to activate fixed inorganic phosphorus, and using the phosphate-solubilizing bacteria can significantly improve the phosphorus activation capacity of soil.

Example 4

Preparation of Microbial Inoculum:

*Paraburkholderia* sp. LSOJM18 monoclonal colonies of example 1 were purified on plates, and inoculated into 5 mL of LB liquid culture medium and cultivated overnight at 28° C. and 180 rpm with shaking. An amount of 1% of inoculum was transferred into 100 mL of LB culture medium, and cultivated at 28° C. and 180 rpm with shaking to the logarithmic growth period. After it was centrifuged at 8,000 rpm for 10 min, the supernatant was discarded and the bacterial colonies were collected. The bacterial colonies were resuspended in sterile water and centrifuged at 8,000 rpm for 10 minutes. This step was repeated 2 to 3 times. The bacterial colonies were finally resuspended in sterile water until the microbial inoculum suspension had OD 600=1.0, the bacterial concentration was about $1 \times 10^9$ CFU/mL.

Example 5

Application of Bacterial Strains in Farmland Ecosystems

A located experiment (43°19'N, 124°14'E) was set up at the conservation tillage experimental base in Lishu County, Siping City, Jilin Province. Before the start of the experiment, the soil had undergone conventional tillage with one crop per annual for many years, and the planting method was mainly maize continuous cropping. The experiment adopted a randomized block design and mainly included 3 treatments, with each treatment repeated 4 times: conventional fertilization (NPK; N: 195 kg/ha., $P_2O_5$: 75 kg/ha., $K_2O$: 90 kg/ha.), 20% reduction in phosphate fertilizer application (NP80K; N: 195 kg/ha., $P_2O_5$: 60 kg/ha., $K_2O$: 90 Kg/ha.)) and 20% reduction in phosphate fertilizer application+microbial inoculum (NP80KL, N: 195 kg/ha., $P_2O_5$: 60 kg/ha., $K_2O$: 90 kg/ha., microbial inoculum prepared in example 3:50 L/ha.). each plot was 70 m2 (7 m×10 m), the growing crop was corn. Crop yield and soil available phosphorus content were measured at harvest time.

1. Measurement of crop yield: during the maturity period of corn, the weight of all spikes within the representative plot S (3 bed width×5 m length as the sampling range, the ridge spacing was recorded to calculate the area) was weighed, and then 10 representative spikes were selected according to the average spike weight method to calculate the seed emergence rate and moisture content, and then the actual yield was calculated based on the sample point area, number of spikes, actual fresh weight, seed emergence rate, and moisture content. Yield-14% moisture content (kg/ha.) =(10000=sample point area)×total number of spikes in sample points×average grain fresh weight per spike sample× (1-sample grain moisture content): (1-14%)×0.85 (note: 0.85 was the production measurement coefficient, used to correct personal errors).

2. Soil sample collection: in each plot of the experimental treatment, after surface debris was removed, soil samples from the 0-10 cm and 10-20 cm soil layers were collected using a earth boring auger with a diameter of 3 cm according to the five-point sampling method. The soil samples from 5 sampling points in the same soil layer were mixed, impurities such as stones and plant roots were removed, then passed through a 2 mm sieve, and mixed evenly into one soil sample. After natural air drying, the soil available phosphorus content was measured.

The results are shown in Table 1:

Table 1 Experimental Results

After the strains were prepared as a microbial inoculum, it can be used as a phosphorus synergistic agent, an activator and an agricultural microbial inoculum. The application of the phosphate-solubilizing bacterium combined with a chemical fertilizer can increase available phosphorus content of soil and fertilizer utilization efficiency, thus reducing the application of phosphate fertilizers by 20% and still ensuring an increase in crop yields by 4.6%, with the available phosphorus contents in the surface soil (0-10 cm) and surface layer (10-20 cm) increased by 9.0% and 12.6%, respectively.

Although the present invention has been described in detail through the above examples, they are only part of the examples of the present invention, rather than all examples, and other examples can also be obtained on basis of these examples without any creative work, all of which belong to the scope of protection of the present invention.

---

---

The invention claimed is:

1. A method of solubilizing and dissolving a calcium phosphate or calcium phytate compound in a composition comprising the calcium phosphate or calcium phytate compound, by contacting the composition with an effective amount of a second composition comprising a purified culture of *Paraburkholderia* sp. LSOJM18, biological deposit no. CCTCCNO: M20222102.

* * * * *

SEQUENCE LISTING

```
Sequence total quantity: 1
SEQ ID NO: 1           moltype = DNA   length = 1437
FEATURE                Location/Qualifiers
source                 1..1437
                       mol_type = other DNA
                       organism = synthetic construct
SEQUENCE: 1
tgcatgcgca tgcttaccat gcagtcgaac ggcagcacgg gagcaatcct ggtggcgagt   60
ggcgaacggg tgagtaatac atcggaacgt gtcctgtagt gggggatagc ccggcgaaag   120
ccggattaat accgcatacg ctctgcggag gaaagcgggg gatccttcgg gacctcgcgc   180
tacaggggcg gccgatggca gattagctag ttggtggggt aaaggcctac caaggcgacg   240
atctgtagct ggtctgagag gacgaccagc cacactggga ctgagacacg gcccagactc   300
ctacgggagg cagcagtggg gaattttgga caatgggcgc aagcctgatc cagcaatgcc   360
gcgtgtgtga agaaggcctt cgggttgtaa agcacttttg tccggaaaga aaaccgcctg   420
gctaatatcc gggtgggatg acggtaccgg aagaataagc accggctaac tacgtgccag   480
cagccgcggt aatacgtagg gtgcaagcgt taatcggaat tactgggcgt aaagcgtgcg   540
caggcggttc gctaagacag atgtgaaatc cccgggctta acctgggaac tgcatttgtg   600
actggcgggc tagagtatgg cagaggggggg tagaattcca cgtgtagcag tgaaatgcgt   660
agagatgtgg aggaataccg atggcgaagg cagccccctg ggccaatact gacgctcatg   720
cacgaaagcg tggggagcaa acaggattag ataccctggt agtccacgcc ctaaacgatg   780
tcaactggtt gtcgggcctt cattggcttg gtaacgtagc taacgcgtga agttgaccgc   840
ctggggagta cggtcgcaag attaaaactc aaaggaattg acggggaccc gcacaagcgg   900
tggatgatgt ggattaattc gatgcaacgc gaaaaacctt acctaccctt gacatgtacg   960
gaaccctgct gagaggtggg ggtgcccgaa agggagccgt aacacaggtg ctgcatggct   1020
gtcgtcagct cgtgtcgtga gatgttgggt taagtcccgc aacgagcgca acccttgtcc   1080
ctagttgcta cgcaagagca ctccaggggag actgccggtg acaaaccgga ggaaggtggg   1140
gatgacgtca agtcctcatg gcccttatgg gtagggcttc acacgtcata caatggtcgg   1200
aacagagggt cgccaagccg cgaggtggag ccaatcccag aaaaccgatc gtagtccgga   1260
tcgcactctg caactcgagt gcgtgaagct ggaatcgcta gtaatcgcgg atcagcatgc   1320
cgcggtgaat acgttcccgg gtcttgtaca caccgcccgt cacaccatgg gagtgggttt   1380
taccagaagt ggctagtcta accgcaagga ggacggtcac cacggtagat caggtca      1437
```